(12) United States Patent
Miyata

(10) Patent No.: US 6,790,617 B1
(45) Date of Patent: Sep. 14, 2004

(54) MEGSIN PROMOTER

(75) Inventor: Toshio Miyata, Isehara (JP)

(73) Assignees: Toshio Miyata, Kanagawa (JP); Kiyoshi Kurokawa, Tokyo (JP)

(*) Notice: Subject to any disclaimer, the term of this patent is extended or adjusted under 35 U.S.C. 154(b) by 0 days.

(21) Appl. No.: 09/889,611

(22) PCT Filed: Jan. 25, 2000

(86) PCT No.: PCT/JP00/00350

§ 371 (c)(1),
(2), (4) Date: Oct. 16, 2001

(87) PCT Pub. No.: WO00/43528

PCT Pub. Date: Jul. 27, 2000

(30) Foreign Application Priority Data

Jan. 25, 1999 (JP) .......................................... 11-015667

(51) Int. Cl.[7] ........................... C12Q 1/68; C12N 15/11
(52) U.S. Cl. .......................................... 435/6; 536/24.1
(58) Field of Search ...................... 435/6, 320.1, 325, 435/419, 243; 536/24.1

(56) References Cited

U.S. PATENT DOCUMENTS 5,558,999 A * 9/1996 Chiang

FOREIGN PATENT DOCUMENTS

| EP | 1018551 | 7/2000 |
|----|---------|--------|
| JP | 6-165679 | 6/1994 |
| WO | WO 99/15652 | 4/1999 |

OTHER PUBLICATIONS

Miyata et al., (1998), *J. Clin. Invest.*, 120(4):828–836.
Miyata et al., (1997), *J. Amer. Soc. Nephrology*, 503A.
Victoria C. Foletta et al., *Journal of Leukocyte Biology*, 63(2):139–152 (Feb. 1998).
Michael G. Rosenfold, *Genes & Development*, 5(6):897–907 (Jun. 1991).

* cited by examiner

*Primary Examiner*—Terry McKelvey
(74) *Attorney, Agent, or Firm*—Karl Bozicevic; Bozicevic, Field & Francis LLP

(57) ABSTRACT

Genomic DNA region including the about 1.5 kb upstream region of MEGSIN gene was isolated and its nucleotide sequence was determined. In the genomic DNA region, two regulatory sequences that regulate the transcription positively were identified. Furthermore, nucleotide substitutions were introduced in the promoter regions located at the 3' sites of the two regulatory sequences by site specific mutagenesis, and the nucleotide sequences that play important roles in the promoter activity were successfully identified.

5 Claims, 9 Drawing Sheets

Figure 1

| | | |
|---|---|---|
| exon II | | |
| megsin | ATTGATAAGgtcag (SEQ ID NO: 35) | tacagTTGCTTCAT (SEQ ID NO: 36) |
| PAI2 | ATGGCCAAGgtgag (SEQ ID NO: 47) | tgcagGTGCTTCAG (SEQ ID NO: 48) |
| exon III | | |
| megsin | AATAGTCAGgtaaa (SEQ ID NO: 37) | aacagTCAGGGCTC (SEQ ID NO: 38) |
| PAI2 | ATTTTGCAGgtatc (SEQ ID NO: 49) | tcaagGCACAAGCT (SEQ ID NO: 50) |
| exon IV | | |
| megsin | TTTCATAAGgtaag (SEQ ID NO: 39) | tatagGACTACATT (SEQ ID NO: 40) |
| PAI2 | TTCCGGGAAgtaag (SEQ ID NO: 51) | aaaagGAATATATT (SEQ ID NO: 52) |
| exon V | | |
| megsin | ACATGgtgag (SEQ ID NO: 41) | aaaagGCAAA (SEQ ID NO: 42) |
| PAI2 | CAAACCAAAGgtaaa (SEQ ID NO: 53) | ctgtagGCAAAATCC (SEQ ID NO: 54) |
| exon IV | | |
| megsin | CCAAGgtatg (SEQ ID NO: 43) | ttcagTGCTC (SEQ ID NO: 44) |
| PAI2 | GTAAACTCGgtatg (SEQ ID NO: 55) | attagGCTCAGCGC (SEQ ID NO: 56) |
| exon IV | | |
| megsin | CTGAAgtaag (SEQ ID NO: 45) | tacagATTGA (SEQ ID NO: 46) |
| PAI2 | TTGGAGCTGgtaag (SEQ ID NO: 57) | tgcagCTGGAAAGT (SEQ ID NO: 58) |

Figure 2

- Promoter region 1431 bp (-1431~-1)
  (SEQ ID NO: 2)
  -1431

```
                a ctttatatcc tcagtaggta agaaatacaa aggatatggg attcaaaata  -1381
ttcagcctat gaacactgca attagaatat ggagaacagg gaatccattt gtaggctcat  -1321
ttttttttta tattaacaac aaccttctcc ttcagaaagt tcaccacaac tgctaaatca  -1261
aaattaaatt tcagggattt tctgcaactt tacttttctc tatgattatt catctcataa  -1201
acaatcatgg aggtgagcaa taactacttt attcgatttt ggataagtta acaggacccc  -1141
cttcttcctg ggaaggaggc aaaattgcac aaaattgaga ggcgagcaac tgtaagatga  -1081
tggtaccttc taattccaat agcttttac aatagagaac ccagttactt ggataaatgt  -1021
tggctgtact tttgaaaaca ctcaggcaga aggaccaggc ttgcagtcat ttccatgcat  -961
agcaggtgaa ggtaggtgca acatacagct caacctcatg atgctacggc cagaaactga  -901
aatgtgtttt tgcccctgtg tggcatgttc tgatggcaaa ggtgtaggca accaactagg  -841
cccaacctac ctttccctac acctggtcac ttttcaaagt gcaaacccac tttaacaaac  -781
tctagcctgt attataggag gaaggatctg ggtggtgcag acgtggcttt ccattgccag  -721
atcagaaggg tggaggagag actggcagga tgacaagaat gaatgaacac accaagtttc  -661
agctcctatc tgaagctgct cagttcaggt aagcatttag agaagccagt tgcaataact  -601
aacagggcaa atgtttctct ggaaaattcc aagccagaga aaattgagaa aagagggaa  -541
ggatggaaag cagtacaaag agaagccagc tcaaaaggtt agaggtccag atgaaaatct  -481
gagattggag aatgataaaa aacattgtgt gagattctat tttaggtcat tatgctaggg  -421
aaatttacac aggatagggt tgaaagaaat taggctataa gatgagtggc aagttgcaat  -361
aaaatggcac cctaaactca ccaagtcact gttgtcactg ctatcttgcc ttagttgatt  -301
tgatgtctag ttagtctatt tgtgtgtttc tcacagaaga gtatgtcttg acccaggctg  -241
acagatactg ttgattctga aatttgtttt tatggttatg ttaaaaccat tgtcattata  -181
agaaacagag atgggaatat tgcctcctga aatctgattc acatacaaac tgaatgaact  -121
acataacaac caccttagtc agatactact ttgaaacctg gttcaaaacc taaatgctta  -61
taagarrctt gagagacagt gctgtgctct gagtcatagg gaagccatcc cagaagccag  -1
```

- 5'-Untranslated region (5'-UTR) 181 bp (+1~+181)
  (SEQ ID NO: 3)

```
gtctacttat caataagcag ctgcctgtgc agagtgcagg ctgcaccttt ggacagcctt   60
taaaactgaa ttctcagaat tttagaacaa attttgtct agaaatgctg actttggttc  120
attaggtagt ggtaaaacag gctcccttcg aagctctcct tcatcacctt cctaagtgca  180
t                                                                181
```

Figure 8
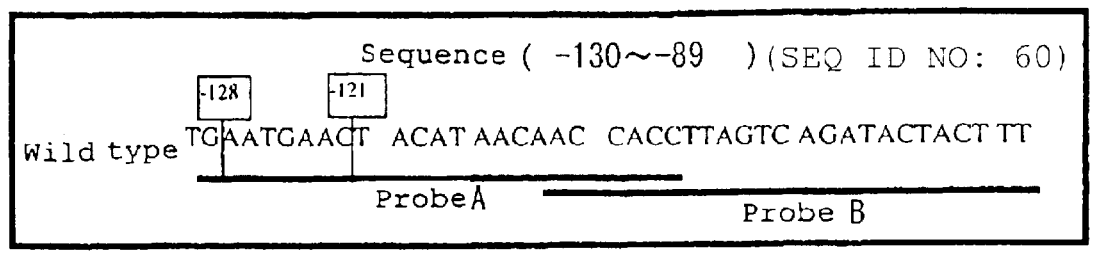
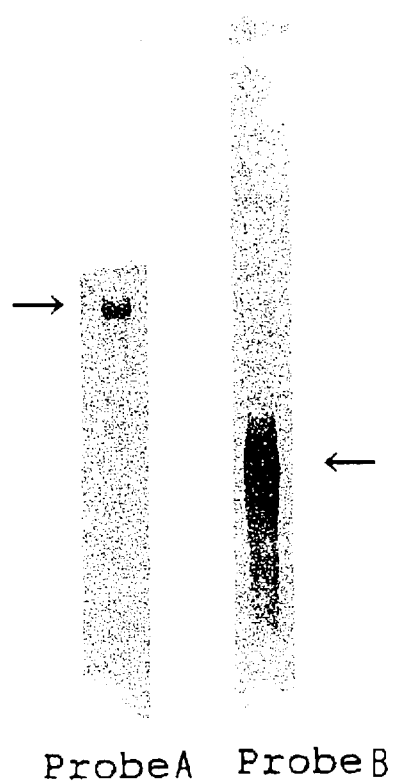

SEQUENCE LISTING

```
<160> NUMBER OF SEQ ID NOS: 60

<210> SEQ ID NO 1
<211> LENGTH: 128
<212> TYPE: DNA
<213> ORGANISM: Homo sapiens

<400> SEQUENCE: 1
aatgaactac ataacaacca ccttagtcag atactacttt gaaacctggt tcaaaaccta      60
aatgcttata agarrcttga gagacagtgc tgtgctctga gtcataggga agccatccca     120
gaagccag                                                              128

<210> SEQ ID NO 2
<211> LENGTH: 1431
<212> TYPE: DNA
<213> ORGANISM: Homo sapiens

<400> SEQUENCE: 2
```

-continued

```
actttatatc ctcagtaggt aagaaataca aaggatatgg gattcaaaat attcagccta      60
tgaacactgc aattagaata tggagaacag ggaatccatt tgtaggctca ttttttttt     120 atattaacaa caaccttctc cttcagaaag ttcaccacaa ctgctaaatc aaaattaaat    180
ttcagggatt ttctgcaact ttacttttct ctatgattat tcatctcata aacaatcatg    240
gaggtgagca ataactactt tattcgattt tggataagtt aacaggaccc ccttcttcct    300
gggaaggagg caaaattgca caaaattgag aggcgagcaa ctgtaagatg atggtacctt    360
ctaattccaa tagcttttta caatagagaa cccagttact tggataaatg ttggctgtac    420
ttttgaaaac actcaggcag aaggaccagg cttgcagtca tttccatgca tagcaggtga    480
aggtaggtgc aacatacagc tcaacctcat gatgctacgg ccagaaactg aaatgtgttt    540
ttgcccctgt gtggcatgtt ctgatggcaa aggtgtaggc aaccaactag cccaaccta    600 cctttcccta cacctggtca cttttcaaag tgcaaaccca ctttaacaaa ctctagcctg    660
tattatagga ggaaggatct gggtggtgca gacgtggctt tccattgcca gatcagaagg    720
gtggaggaga gactggcagg atgacaagaa tgaatgaaca caccaagttt cagctcctat    780
ctgaagctgc tcagttcagg taagcattta gagaagccag ttgcaataac taacagggca    840
aatgtttctc tggaaaattc caagccagag aaaattgaga aaagaggga aggatggaaa     900 gcagtacaaa gagaagccag ctcaaaaggt tagaggtcca gatgaaaatc tgagattgga    960
gaatgataaa aaacattgtg tgagattcta ttttaggtca ttatgctagg gaaatttaca   1020
caggataggg ttgaaagaaa ttaggctata agatgagtgg caagttgcaa taaaatggca   1080
ccctaaactc accaagtcac tgttgtcact gctatcttgc cttagttgat ttgatgtcta   1140
gttagtctat ttgtgtgttt ctcacagaag agtatgtctt gacccaggct gacagatact   1200
gttgattctg aaatttgttt ttatggttat gttaaaacca ttgtcattat aagaaacaga   1260
gatgggaata ttgcctcctg aaatctgatt cacatacaaa ctgaatgaac tacataacaa   1320
ccaccttagt cagatactac tttgaaacct ggttcaaaac ctaaatgctt ataagarrct   1380
tgagagacag tgctgtgctc tgagtcatag ggaagccatc ccagaagcca g            1431
```

<210> SEQ ID NO 3
<211> LENGTH: 181
<212> TYPE: DNA
<213> ORGANISM: Homo sapiens
<220> FEATURE:
<221> NAME/KEY: 5'UTR
<222> LOCATION: (1)..(181)
<223> OTHER INFORMATION:

<400> SEQUENCE: 3

```
gtctacttat caataagcag ctgcctgtgc agagtgcagg ctgcaccttt ggacagcctt      60
taaaactgaa ttctcagaat ttagaacaa attttgtct agaaatgctg actttggttc      120
attaggtagt ggtaaaacag gctcccttcg aagctctcct tcatcacctt cctaagtgca    180
t                                                                    181
```

<210> SEQ ID NO 4
<211> LENGTH: 28
<212> TYPE: DNA
<213> ORGANISM: Artificial
<220> FEATURE:
<223> OTHER INFORMATION: an artificially synthesized primer sequence

<400> SEQUENCE: 4

```
cgtcgacgga cacgtctcac gtccgacg                                        28
```

```
<210> SEQ ID NO 5
<211> LENGTH: 31
<212> TYPE: DNA
<213> ORGANISM: Artificial
<220> FEATURE:
<223> OTHER INFORMATION: an artificially synthesized primer sequence

<400> SEQUENCE: 5
ttccctgtac atgcacttag gaaggtgatg a                              31

<210> SEQ ID NO 6
<211> LENGTH: 29
<212> TYPE: DNA
<213> ORGANISM: Artificial
<220> FEATURE:
<223> OTHER INFORMATION: an artificially synthesized primer sequence

<400> SEQUENCE: 6
ggtaccttct aattccaata gctttttac                                 29

<210> SEQ ID NO 7
<211> LENGTH: 30
<212> TYPE: DNA
<213> ORGANISM: Artificial
<220> FEATURE:
<223> OTHER INFORMATION: an artificially synthesized primer sequence

<400> SEQUENCE: 7
ccagttactt ggataaatgt tggctgtact                                30

<210> SEQ ID NO 8
<211> LENGTH: 30
<212> TYPE: DNA
<213> ORGANISM: Artificial
<220> FEATURE:
<223> OTHER INFORMATION: an artificially synthesized primer sequence

<400> SEQUENCE: 8
ctcaggcaga aggaccaggc ttgcagtcat                                30

<210> SEQ ID NO 9
<211> LENGTH: 30
<212> TYPE: DNA
<213> ORGANISM: Artificial
<220> FEATURE:
<223> OTHER INFORMATION: an artificially synthesized primer sequence

<400> SEQUENCE: 9
acatacagct caacctcatg atgctacggc                                30

<210> SEQ ID NO 10
<211> LENGTH: 30
<212> TYPE: DNA
<213> ORGANISM: Artificial
<220> FEATURE:
<223> OTHER INFORMATION: an artificially synthesized primer sequence

<400> SEQUENCE: 10
cctcatgatg ctacggccag aaactgaaat                                30

<210> SEQ ID NO 11
<211> LENGTH: 30
<212> TYPE: DNA
<213> ORGANISM: Artificial
<220> FEATURE:
```

<223> OTHER INFORMATION: an artificially synthesized primer sequence

<400> SEQUENCE: 11
ccaagtttca gctcctatct gaagctgctc                                  30

<210> SEQ ID NO 12
<211> LENGTH: 30
<212> TYPE: DNA
<213> ORGANISM: Artificial
<220> FEATURE:
<223> OTHER INFORMATION: an artificially synthesized primer sequence

<400> SEQUENCE: 12
ggtccagatg aaaatctgag attggagaat                                  30

<210> SEQ ID NO 13
<211> LENGTH: 30
<212> TYPE: DNA
<213> ORGANISM: Artificial
<220> FEATURE:
<223> OTHER INFORMATION: an artificially synthesized primer sequence

<400> SEQUENCE: 13
atgtcttgac ccaggctgac agatactgtt                                  30

<210> SEQ ID NO 14
<211> LENGTH: 30
<212> TYPE: DNA
<213> ORGANISM: Artificial
<220> FEATURE:
<223> OTHER INFORMATION: an artificially synthesized primer sequence

<400> SEQUENCE: 14
cctcctgaaa tctgattcac atacaaactg                                  30

<210> SEQ ID NO 15
<211> LENGTH: 30
<212> TYPE: DNA
<213> ORGANISM: Artificial
<220> FEATURE:
<223> OTHER INFORMATION: an artificially synthesized primer sequence

<400> SEQUENCE: 15
aatgaactac ataacaacca ccttagtcag                                  30

<210> SEQ ID NO 16
<211> LENGTH: 30
<212> TYPE: DNA
<213> ORGANISM: Artificial
<220> FEATURE:
<223> OTHER INFORMATION: an artificially synthesized primer sequence

<400> SEQUENCE: 16
tacataacaa ccaccttagt cagatactac                                  30

<210> SEQ ID NO 17
<211> LENGTH: 30
<212> TYPE: DNA
<213> ORGANISM: Artificial
<220> FEATURE:
<223> OTHER INFORMATION: an artificially synthesized primer sequence

<400> SEQUENCE: 17
tactactttg aaacctggtt caaaacctaa                                  30

```
<210> SEQ ID NO 18
<211> LENGTH: 30
<212> TYPE: DNA
<213> ORGANISM: Artificial
<220> FEATURE:
<223> OTHER INFORMATION: an artificially synthesized primer sequence

<400> SEQUENCE: 18
aggctgtcca aaggtgcagc ctgcactctg                                    30

<210> SEQ ID NO 19
<211> LENGTH: 23
<212> TYPE: DNA
<213> ORGANISM: Artificial
<220> FEATURE:
<223> OTHER INFORMATION: an artificially synthesized oligonucleotide
      sequence

<400> SEQUENCE: 19
gaatgaacta cataacaacc acc                                           23

<210> SEQ ID NO 20
<211> LENGTH: 25
<212> TYPE: DNA
<213> ORGANISM: Artificial
<220> FEATURE:
<223> OTHER INFORMATION: an artificially synthesized oligonucleotide
      sequence

<400> SEQUENCE: 20
aaccacctta gtcagatact acttt                                         25

<210> SEQ ID NO 21
<211> LENGTH: 10
<212> TYPE: DNA
<213> ORGANISM: Homo sapiens

<400> SEQUENCE: 21
ctagcgtgag                                                          10

<210> SEQ ID NO 22
<211> LENGTH: 10
<212> TYPE: DNA
<213> ORGANISM: Homo sapiens

<400> SEQUENCE: 22
tctaggctgc                                                          10

<210> SEQ ID NO 23
<211> LENGTH: 10
<212> TYPE: DNA
<213> ORGANISM: Homo sapiens

<400> SEQUENCE: 23
ataaggtcag                                                          10

<210> SEQ ID NO 24
<211> LENGTH: 10
<212> TYPE: DNA
<213> ORGANISM: Homo sapiens

<400> SEQUENCE: 24
tacagttgct                                                          10

<210> SEQ ID NO 25
```

```
<211> LENGTH: 10
<212> TYPE: DNA
<213> ORGANISM: Homo sapiens

<400> SEQUENCE: 25
gtcaggtaaa                                                            10

<210> SEQ ID NO 26
<211> LENGTH: 10
<212> TYPE: DNA
<213> ORGANISM: Homo sapiens

<400> SEQUENCE: 26
aacagtcagg                                                            10

<210> SEQ ID NO 27
<211> LENGTH: 10
<212> TYPE: DNA
<213> ORGANISM: Homo sapiens

<400> SEQUENCE: 27
ataaggtaag                                                            10

<210> SEQ ID NO 28
<211> LENGTH: 10
<212> TYPE: DNA
<213> ORGANISM: Homo sapiens

<400> SEQUENCE: 28
tataggacta                                                            10

<210> SEQ ID NO 29
<211> LENGTH: 10
<212> TYPE: DNA
<213> ORGANISM: Homo sapiens

<400> SEQUENCE: 29
acatggtgag                                                            10

<210> SEQ ID NO 30
<211> LENGTH: 10
<212> TYPE: DNA
<213> ORGANISM: Homo sapiens

<400> SEQUENCE: 30
aaaaggcaaa                                                            10

<210> SEQ ID NO 31
<211> LENGTH: 10
<212> TYPE: DNA
<213> ORGANISM: Homo sapiens

<400> SEQUENCE: 31
ccaaggtatg                                                            10

<210> SEQ ID NO 32
<211> LENGTH: 10
<212> TYPE: DNA
<213> ORGANISM: Homo sapiens

<400> SEQUENCE: 32
ttcagtgctc                                                            10
```

```
<210> SEQ ID NO 33
<211> LENGTH: 10
<212> TYPE: DNA
<213> ORGANISM: Homo sapiens

<400> SEQUENCE: 33
ctgaagtaag                                                          10

<210> SEQ ID NO 34
<211> LENGTH: 10
<212> TYPE: DNA
<213> ORGANISM: Homo sapiens

<400> SEQUENCE: 34
tacagattga                                                          10

<210> SEQ ID NO 35
<211> LENGTH: 14
<212> TYPE: DNA
<213> ORGANISM: Homo sapiens

<400> SEQUENCE: 35
attgataagg tcag                                                     14

<210> SEQ ID NO 36
<211> LENGTH: 14
<212> TYPE: DNA
<213> ORGANISM: Homo sapiens

<400> SEQUENCE: 36
tacagttgct tcat                                                     14

<210> SEQ ID NO 37
<211> LENGTH: 14
<212> TYPE: DNA
<213> ORGANISM: Homo sapiens

<400> SEQUENCE: 37
aatagtcagg taaa                                                     14

<210> SEQ ID NO 38
<211> LENGTH: 14
<212> TYPE: DNA
<213> ORGANISM: Homo sapiens

<400> SEQUENCE: 38
aacagtcagg gctc                                                     14

<210> SEQ ID NO 39
<211> LENGTH: 14
<212> TYPE: DNA
<213> ORGANISM: Homo sapiens

<400> SEQUENCE: 39
tttcataagg taag                                                     14

<210> SEQ ID NO 40
<211> LENGTH: 14
<212> TYPE: DNA
<213> ORGANISM: Homo sapiens

<400> SEQUENCE: 40
tataggacta catt                                                     14
```

```
<210> SEQ ID NO 41
<211> LENGTH: 10
<212> TYPE: DNA
<213> ORGANISM: Homo sapiens

<400> SEQUENCE: 41
acatggtgag                                                            10

<210> SEQ ID NO 42
<211> LENGTH: 10
<212> TYPE: DNA
<213> ORGANISM: Homo sapiens

<400> SEQUENCE: 42
aaaaggcaaa                                                            10

<210> SEQ ID NO 43
<211> LENGTH: 10
<212> TYPE: DNA
<213> ORGANISM: Homo sapiens

<400> SEQUENCE: 43
ccaaggtatg                                                            10

<210> SEQ ID NO 44
<211> LENGTH: 10
<212> TYPE: DNA
<213> ORGANISM: Homo sapiens

<400> SEQUENCE: 44
ttcagtgctc                                                            10

<210> SEQ ID NO 45
<211> LENGTH: 10
<212> TYPE: DNA
<213> ORGANISM: Homo sapiens

<400> SEQUENCE: 45
ctgaagtaag                                                            10

<210> SEQ ID NO 46
<211> LENGTH: 10
<212> TYPE: DNA
<213> ORGANISM: Homo sapiens

<400> SEQUENCE: 46
tacagattga                                                            10

<210> SEQ ID NO 47
<211> LENGTH: 14
<212> TYPE: DNA
<213> ORGANISM: Homo sapiens

<400> SEQUENCE: 47
atggccaagg tgag                                                       14

<210> SEQ ID NO 48
<211> LENGTH: 14
<212> TYPE: DNA
<213> ORGANISM: Homo sapiens

<400> SEQUENCE: 48
tgcaggtgct tcag                                                       14
```

```
<210> SEQ ID NO 49
<211> LENGTH: 14
<212> TYPE: DNA
<213> ORGANISM: Homo sapiens

<400> SEQUENCE: 49
attttgcagg tatc                                                        14

<210> SEQ ID NO 50
<211> LENGTH: 14
<212> TYPE: DNA
<213> ORGANISM: Homo sapiens

<400> SEQUENCE: 50
tcaaggcaca agct                                                        14

<210> SEQ ID NO 51
<211> LENGTH: 14
<212> TYPE: DNA
<213> ORGANISM: Homo sapiens

<400> SEQUENCE: 51
ttccgggaag taag                                                        14

<210> SEQ ID NO 52
<211> LENGTH: 14
<212> TYPE: DNA
<213> ORGANISM: Homo sapiens

<400> SEQUENCE: 52
aaaaggaata tatt                                                        14

<210> SEQ ID NO 53
<211> LENGTH: 15
<212> TYPE: DNA
<213> ORGANISM: Homo sapiens

<400> SEQUENCE: 53
caaaccaaag gtaaa                                                       15

<210> SEQ ID NO 54
<211> LENGTH: 15
<212> TYPE: DNA
<213> ORGANISM: Homo sapiens

<400> SEQUENCE: 54
ctgtaggcaa aatcc                                                       15

<210> SEQ ID NO 55
<211> LENGTH: 14
<212> TYPE: DNA
<213> ORGANISM: Homo sapiens

<400> SEQUENCE: 55
gtaaactcgg tatg                                                        14

<210> SEQ ID NO 56
<211> LENGTH: 14
<212> TYPE: DNA
<213> ORGANISM: Homo sapiens

<400> SEQUENCE: 56
```

```
attaggctca gcgc                                                        14

<210> SEQ ID NO 57
<211> LENGTH: 14
<212> TYPE: DNA
<213> ORGANISM: Homo sapiens

<400> SEQUENCE: 57
ttggagctgg taag                                                        14

<210> SEQ ID NO 58
<211> LENGTH: 14
<212> TYPE: DNA
<213> ORGANISM: Homo sapiens

<400> SEQUENCE: 58
tgcagctgga aagt                                                        14

<210> SEQ ID NO 59
<211> LENGTH: 40
<212> TYPE: DNA
<213> ORGANISM: Homo sapiens

<400> SEQUENCE: 59
tgaatgaact acataacaac caccttagtc agatactact                            40

<210> SEQ ID NO 60
<211> LENGTH: 42
<212> TYPE: DNA
<213> ORGANISM: Homo sapiens

<400> SEQUENCE: 60
tgaatgaact acataacaac caccttagtc agatactact tt                         42
```

MEGSIN PROMOTER

CROSS-REFERENCES

This application is a national stage filing under 35 U.S.C. §371 of PCT/JP00/00350 filed Jan. 25, 2000 which International Application was published by the International Bureau in English on Jul. 27, 2000 which claims priority to Japanese Patent Application No. 11/15667 filed Jan. 25, 1999.

TECHNICAL FIELD

The present invention relates to a promoter of a gene expressed in renal cells. The promoter of this invention can be applied to the field such as gene therapy.

BACKGROUND ART

Sixty trillion various cells in a living body have essentially identical genomic DNA. For the normal physiological functions, the expression of these genes is strictly controlled through signals received by cell lines and cells. Therefore, elucidation of genes expressed specifically in each cell type is very important.

Mesangium is located in the center of lobula of capillary loop in glomerulus and is a tissue of a core that connects each lobule. Mesangium is covered by glomerular basal membrane and comprises mesangial cells which are separated from capillary cavity by endothelial cells and amorphous material (mesangial matrix) which is continuous with internal hyaline layer in glomerular basal membarane consisting of three layers.

A mesangial cell is known to play a pivotal role in maintaining the structure and function of a glomerulus and is considered to be the major cause of the onset of glomerular diseases such as glomerulonephritis and glomerulosclerosis. A mesangial cell is a target of disorders for each type of nephritis. For example, proliferation of mesangial cells and accumulation of extracellular mesangial matrix are thought to be the first step in which glomerulosclerosis is developed in a patient suffering from various glomerular diseases such as chronic glomerulonephritis and diabetic nephropathy, the two major causes of the end stage of renal failure [D. Schlondorff, Kidney Int., 49, 1583–1585 (1996); R. B. Sterzel et al., Glomerular mesangial cells. Immunologic Renal Diseases, pp595–626 (1997)]. Therefore, identification of genes expressed specifically in mesangial cells and elucidation of mechanism regulating its expression are helpful for understanding biological characteristics of mesangial cells and the causes of diseases relating to mesangial cells, and in turn, treating or diagnosing diseases relating to mesangial cells.

Through the determination of large-scale DNA sequences and through the database analysis, the present inventor isolated a gene named MEGSIN that is strongly expressed specifically in mesangial cells. The inventor also determined the whole nucleotide sequence of the gene and deduced the amino acid sequence of the novel protein (human MEGSIN) comprising 380 amino acids encoded by the whole cDNA clone of MEGSIN. Furthermore, the homology search in amino acid sequences with FASTA program using SwissProt database revealed that human MEGSIN belonged to SERPIN (serine protease inhibitor) superfamily [R. Carrell et al., Trends Biochem. Sci., 10, 20 (1985); R. Carrell et al., Cold Spring Harbor Symp. Quant. Biol., 52, 527 (1987); E. K. O. Kruithof et al., Blood, 86, 4007 (1995); J. Potempa et al., J. Biol. Chem., 269, 15957 (1994); E. Remold-O'Donnell, FEBS Lett., 315, 105 (1993)] [T. Miyata et al., J. Clin. Invest., 120, 828–836 (1998)].

Human MEGSIN is weakly expressed in human fibroblasts, smooth muscle cells, endothelial cells, and keratinocytes, but is strongly expressed in mesangial cells (that means human MEGSIN gene is expressed specifically in mesangial cells). When compared between IgA nephropathy patients or diabetic nephropathy patients and normal healthy people, the expression level of MEGSIN in renal tissue is significantly larger in IgA nephropathy patients or diabetic nephropathy patients [D. Suzuki et al., J. Am. Soc. Nephrol. 10, 2606–2613 (1999)]. Also, increase in expression level was observed in the model of mesangial proliferative glomerulonephritis using rats.

As indicated above, there is a possibility that the expression of MEGSIN gene is deeply involved in renal disease. Therefore, it is desired to reveal the actual condition of the regulatory mechanisms of the expression of MEGSIN gene, to clarify the function of human MEGSIN in vivo, and to provide useful promoter that is available for diagnosis and treatment of, for example, genetic disease caused by the mutation of MEGSIN or that expresses specifically in mesangial cells.

On the other hand, because the members of SERPIN superfamily to which human MEGSIN belongs are highly similar to each other in their primary structures, they are thought to be derived from the evolutionary common ancestral protein. Namely, as a result of the analysis of the phylogenetic tree constructed based on the number of mutated amino acids in the sequences [K. Suzuki et al., Tanpakushitsu Kakusan Koso, 34, 949–962 (1989)] and on the chromosomal gene structure [J. J. Bao et al., Biochem., 26, 7755 (1987)], it has been revealed that SERPIN superfamily has evolved through not less than 5 million years with various higher vertebrates. It is extreme characteristic of MEGSIN gene that it is expressed specifically in mesangial cells in glomerulus.

Recently, it was reported that genes of ion channels and genes involved in transportation are expressed specifically in kidney [S. J. Lolait et al., Nature, 357, 336–339 (1992); Y. Kanai et al., J. Clin. Invest., 93, 397–404 (1994); S. Uchida et al., J. Biol. Chem., 268, 3821–3824 (1993); S. Adachi et al., J. Biol. Chem., 269, 17677–17683 (1994); K. Fushimi et al., Nature, 361, 549–552 (1993); G. Gamba et al., J. Biol. Chem., 269, 17713–17722 (1994)].

However, these genes are located in epithelial cells of renal tubular and are not expressed in mesangial cells of glomeruli. Therefore, identification of the promoter and the transcription factors of MEGSIN gene can bring important information about the mechanism of gene expression depending on specific cell type. This information can also be applied to target cells in molecular genetics and gene transfer.

DISCLOSURE OF THE INVENTION

An objective of this invention is to provide a promoter of MEGSIN gene and its use.

The present inventor has determined nucleotide sequences of genomic DNA which is about 1.5 kb long including the upstream (5' terminal) sequences of MEGSIN gene to reveal the regulatory mechanism of expression of MEGSIN gene. As a result of S1 nuclease protection assay, it has been revealed that four transcription initiation sites are existed in MEGSIN mRNA. It has also been revealed that the conserved transcription regulatory sequence that can be the transcription regulatory sites including AP1 binding site, cMyb binding site, and Oct-1 exist upstream of the transcription initiation site. Vectors in which various region of this transcription regulatory sequence were deleted and luciferase gene was integrated into the 3' region have been constructed and the transcription regulatory region has been determined by detecting luciferase activity in cells transfected with the vector. As a result, two regulatory sequences have been identified that control transcription positively. The transcription regulatory activity of one promoter region that is located at 3' end has been analyzed in detail by introducing nucleotide substitution based on the method of site specific mutagenesis. As a result, the present inventor has succeeded in determining the nucleotide sequence of the DNA that plays an important role in transcriptional regulation.

Therefore, the present invention relates to a promoter of MEGSIN gene and its use, and more specifically relates to the following:
(1) a DNA comprising the nucleotide sequence of SEQ ID NO: 1 or a part thereof, the DNA having a promoter activity;
(2) a vector comprising the DNA of (1);
(3) the vector of (2), wherein a foreign gene is expressibly ligated downstream of the DNA of (1);,
(4) a cell transfected with the vector of (3);
(5) a method for screening a protein that binds to a DNA comprising the nucleotide sequence of SEQ ID NO: 1 or a part thereof, the method comprising the steps of: (a) contacting a test sample with the DNA comprising the nucleotide sequence of SEQ ID NO: 1 or a part thereof, and (b) selecting a protein that has an activity to bind the DNA comprising the nucleotide sequence of SEQ ID NO: 1 or a part thereof;
(6) a protein that can be isolated by the method of (5); and
(7) the protein of (6), wherein the protein is a transcription factor.

Herein, "promoter" indicates the DNA region that exists near transcription initiation site and that controls the expression of a gene. In addition, "promoter activity" indicates the activity of the promoter that controls the expression of a gene that exists downstream of the promoter.

The present invention provides a promoter of MEGSIN gene. As indicated in Example 3, the deletion or substitution of the nucleotide existing downstream of −128th position in the 5' upstream region of MEGSIN gene often shows remarkable decrease in promoter activity. Thus, the promoter of this invention includes at least a part of 5' upstream region of MEGSIN gene that is downstream of −128th position (SEQ ID NO: 1).

The promoter of this invention may have the nucleotide sequence of SEQ ID NO: 1 in which one or more nucleotides are substituted, as long as it includes at least a part of the region downstream of −128th position (SEQ ID NO: 1) and as long as it has a promoter activity. However, as indicated FIG. 7, mutations in the downstream region of −128th position: m1 mutation (nucleotide substitutions at −128th and −127th positions), m2 mutation (nucleotide substitutions at −120th, −118th, and −117th positions), m3 mutation (nucleotide substitutions at −116th and −115th positions), m4 mutation (nucleotide substitutions at −113th and −112th positions), m5 mutation (nucleotide substitutions at −106th and −105th positions), m6 mutation (nucleotide substitutions at −100th and −98th positions), and m7 mutation (nucleotide substitutions at −94th and −93rd positions) cause the decline of promoter activity.

Therefore, substitutions of these nucleotides are not preferred when the high promoter activity is required.

The promoter of this invention can be isolated by the method such as screening of a genomic DNA library. That is, the promoter can be isolated by hybridization screening of a genomic DNA library of human or other animals using the known MEGSIN cDNA or a part thereof as a probe or by polymerase chain reaction (PCR) using the primers that is designed based on the sequence of MEGSIN cDNA or MEGSIN genomic DNA and using a genomic DNA library of human or other animals as a template.

The promoter of this invention can also be produced by following the standard methods using chemical synthesis of nucleic acids, such as phosphoamidide method [Mattencci, M. D. & Caruthers, M. H. J. Am. Chem. Soc. 103, 3185 (1981)] and phosphite triester method [Hunkapiller, M. et al., Nature 310, 105 (1984)].

The promoter region and the enhancer region (existing in an intron or 3' noncoding region and including the DNA region that promotes the expression of the gene) of MEGSIN gene existing in the DNA fragments can be obtained, for example, by the same method described in Unexamined Published Japanese Patent Application (JP-A) No. Hei 6-181767 or in the reference [The Journal of Immunology (1995) 155, 2477–2486, Proc. Natl. Acad. Sci. USA (1995) 92, 3561–3565].

In general, the presence or the strength of the promoter activity can be judged by expressibly ligating, downstream of an candidate promoter, the gene (reporter gene) encoding the protein that can easily determined quantitatively by, for example, color or luminescent reaction, by transfecting a host cell with it, and by detecting the color or luminescent reaction.

Specifically, a promoter region can be obtained by the following method but not limited thereto.
1) DNA including transcription regulatory region from genomic DNA or a genomic library as indicated above is cloned.
2) MEGSIN gene is digested with restriction enzyme to obtain a DNA containing a translation initiation codon of MEGSIN gene and comprising the promoter region (2 to 5 kbp) upstream thereof, and to determine the nucleotide sequence. The transcription initiation site (+1) is determined using, as a template, poly(A)$^+$ RNA prepared from mesangial cells and such by the primer elongation method using primer DNA selected from cDNA sequence at 5' end site of MEGSIN gene. A site possibly comprising the promoter activity is predicted by searching transcription factor binding sequence from the nucleotide sequence.
3) The DNA fragment excluding the coding region of MEGSIN gene from the DNA obtained in 2) is subcloned in a plasmid, and reporter gene (for example, chloramphenicol acetyl transferase (CAT) gene or a luciferase gene etc.) is ligated downstream of the 2 to 5 kbp DNA fragment to construct a reporter plasmid. Similarly, DNA fragments corresponding to various sites upstream of MEGSIN gene, in which 5' and 3' end sites are stepwise removed, are prepared by digestion with restriction enzymes or by PCR and such to include possible promoter regions. A reporter gene is ligated downstream of these DNA fragments to construct a reporter plasmid. A DNA fragment in which one or more nucleotides are appropriately replaced, deleted, added, and/or inserted by site specific mutagenesis is prepared. A reporter plasmid is constructed in which a reporter gene is ligated downstream of the DNA fragment.
4) A promoter region existing at the upstream region of MEGSIN gene is identified by measuring the reporter activity (for example, CAT activity or luciferase activity etc.) in animal cells that is transformed with the reporter plasmid constructed in 3).

An enhancer region existing in 3' noncoding region or an intron can be identified by, for example, screening, as a probe, a genomic library with the MEGSIN cDNA and such, cloning MEGSIN genomic DNA, and conducting the experiment in the same method as that in the case of the promoter above.

A promoter of this invention has an activity to highly express a gene ligated downstream thereof in kidney (mesangial cells). Thus, the promoter of this invention can be used, for example, to develop a vector that can control the expression of desired genes in kidney. The promoter of this invention can also be expected to have the same effect in other cells (or organs) that has transcription factors that activate the promoter of this invention. Such promoter as is activated specifically in kidney can be used, for example, for constructing vectors for gene therapy of renal disease.

When the promoter of this invention is used for the kidney-specific expression of a gene, desired gene to be expressed in kidney is expressibly ligated downstream of the promoter, and is introduced into a target cell. The phrase "expressibly ligated" indicates that the gene is ligated to the promoter of this invention so that its expression is possible.

When a promoter of this invention and a gene controlled by the promoter are introduced into a target cell, they can be integrated into any appropriate vectors. The promoter of this invention can be used alone or in association with transcription regulatory sequences such as enhancer and silencer.

Vectors derived from, for example, retrovirus, herpes simplex virus, cytomegalovirus, Epstein-Barr virus, bovine papillomavirus, adenovirus, adeno associated virus, sindbis virus, and poxvirus can be used for gene therapy. Formulation of liposome such as thermosensitive liposome, blood stable liposome, cationic liposome, pH dependent liposome, rearranged liposome including a envelope protein of virus, and such; formulation of membrane fusion liposome, which has membrane fusion ability of virus, such as HVJ (Sendai virus)-liposome [T. Nakagawa et al., Drug Delivery System, 11, 411 (1996)], VSV (vesicular stomatitis virus)-liposome (Japanese Patent Application No. Hei 9-357506), and such; and so on are also available.

Target cells into which the vectors are introduced can be, for example, mesangial cells, renal tubule cells, macrophage, lymphocyte, endothelial cells, and tumor cells.

Besides the methods described above, general gene manipulations for preparing the promoter of this invention and recombinant vector having the promoter and for transfecting a cell with the vector and such can be conducted by following, for example, the standard methods described in "Molecular Cloning—A Laboratory Manual" (Cold Spring Harbor Laboratory, N.Y.).

Because mutations in the promoter of this invention may cause serious genetic disease, the promoter is expectedly applicable to gene diagnosis. This gene diagnosis can be achieved by, for example, detecting the mutation by direct sequencing using the method such as single strand conformational polymorphism, DNA fingerprinting method, and PCR method, by mutation analysis using gene-specific oligonucleotide probe, etc.

Because human MEGSIN belongs to SERPIN superfamily, the disorder of human MEGSIN can cause thromboembolism by promoting the ability of blood clotting and hemorrhagic disease by promoting the ability of fibrinolysis [Suzuki et al., Tanpakushitsu Kakusan Kouso, 34, 949–962 (1989)]. This suggests that drugs affecting the transcription activity of the promoter of this invention can act on onset or repression of these diseases. Therefore, the promoter of this invention can be used for the screening of drugs for these diseases.

Because the expression level of MEGSIN is promoted in IgA nephropathy patients and diabetic nephropathy patients, it is thought to be involved in onset of renal disease. Therefore, onset or promotion of IgA nephropathy and diabetic nephropathy can be repressed by administering, to the patients, drugs that control the promoter activity of this invention.

This invention relates to the method for screening a protein that binds to the promoter of this invention. A protein that binds to the promoter of this invention is, for example, a transcription factor. "A transcription factor" indicates a protein that binds to the promoter of this invention and regulates positively or negatively the expression of a gene existing downstream of the promoter.

The screening method of this invention includes the steps of: (a) contacting a test sample with the DNA comprising the nucleotide sequence of SEQ ID NO: 1 or part thereof and (b) selecting a protein that has an activity to bind the DNA comprising the nucleotide sequence of SEQ ID NO: 1 or a part thereof.

The screening method of this invention can be conducted by the known method to one skilled in the art [referred to Shin Saibou Kougaku Jikken Purotokoru (New Cell Engineering Experiment Protocol), Shujun-sha; Biomanual series 5 Tensha Inshi Kenkyu-hou (method for studying transcription factors), Yodo-sha; and DNA & Cell Biology, 13, 731–742 (1994)], for example, a method using affinity column, Southwestern method, footprinting method, gel shift method, and one-hybrid method.

The affinity column method can be performed by applying a nucleic extract onto an column in which the promoter of this invention obtained in the above manner are immobilized on Sepharose or latex beads, washing the column, and eluting the binding transcription factor using a DNA comprising the same sequence as that immobilized in the column.

In the case of Southwestern method, for example, cDNA is constructed from mRNA derived from the cells in which a transcription factor that binds to the promoter of this invention is expected to be expressed (for example, mesangial cells). Then, the cDNA is integrated into an *E. coli* expression vector, such as λgt11, to construct a cDNA library, and a fusion protein with β-galactosidase is synthesized. The fusion protein is adsorbed on a nitrocellulose membrane, and a phage that synthesizes the fusion protein showing binding activities is selected using, as a probe, a radiolabeled DNA fragment of the promoter of this invention.

In the case of footprinting method, DNA sequence that binds to protein can be determined by using radiolabeled promoter as probe, mixed it with a nuclear extract, digesting it by DNase I, and conducting electrophoresis.

In the case of gel shift method, a probe is constructed from a sequence in the promoter region, and radiolabeled. Then, the radiolabeled probe and a nuclear extract are mixed, and electrophoresed to determine presence or absence of a nuclear protein that binds to the probe.

In the case of one-hybrid method, for example, sequence that contains tandem repeats of at least 3 copies of MEGSIN promoter sequence are ligated upstream of the reporter gene, and then integrated into the yeast genome to construct reporter strain. The above cDNA is ligated to the coding region for activation domain of GAL4 (transcription activating factor binding to DNA of yeast) (GAL4 AD), and the activation domain (AD) libraries that encode this fusion protein are constructed and introduced into the reporter strain above. Binding of the hybrid protein of AD and a DNA binding protein that binds to the MEGSIN promoter sequence activates the transcription. The effect can be detected by the expression of the reporter gene.

BRIEF DESCRIPTION OF THE DRAWINGS

FIG. 1 shows the comparison of the boundaries between exon and intron of human MEGSIN gene with that of PAI-2 gene. Upper-case characters indicate exons and lower-case characters indicate introns.

FIG. 2 shows the sequence of first exon (5'-UTR) of human MEGSIN gene and of the upstream 1431 bp sequence. 5' terminus of the clone obtained by 5' RACE is indicated as "*".

Promoter, none; enhancer, none; SV40 late polyA signal, 1772–1993; luciferase gene (luc+), 88–1737; upstream polyA signal, 4658–4811; multiple cloning site, 1–58; β-lactamase gene (Amp$^r$), 3940–3083; the f1 origin of replication, 4073–4527; the origin of replication of the plasmid derived from ColE1, 2313.

Figure 5:
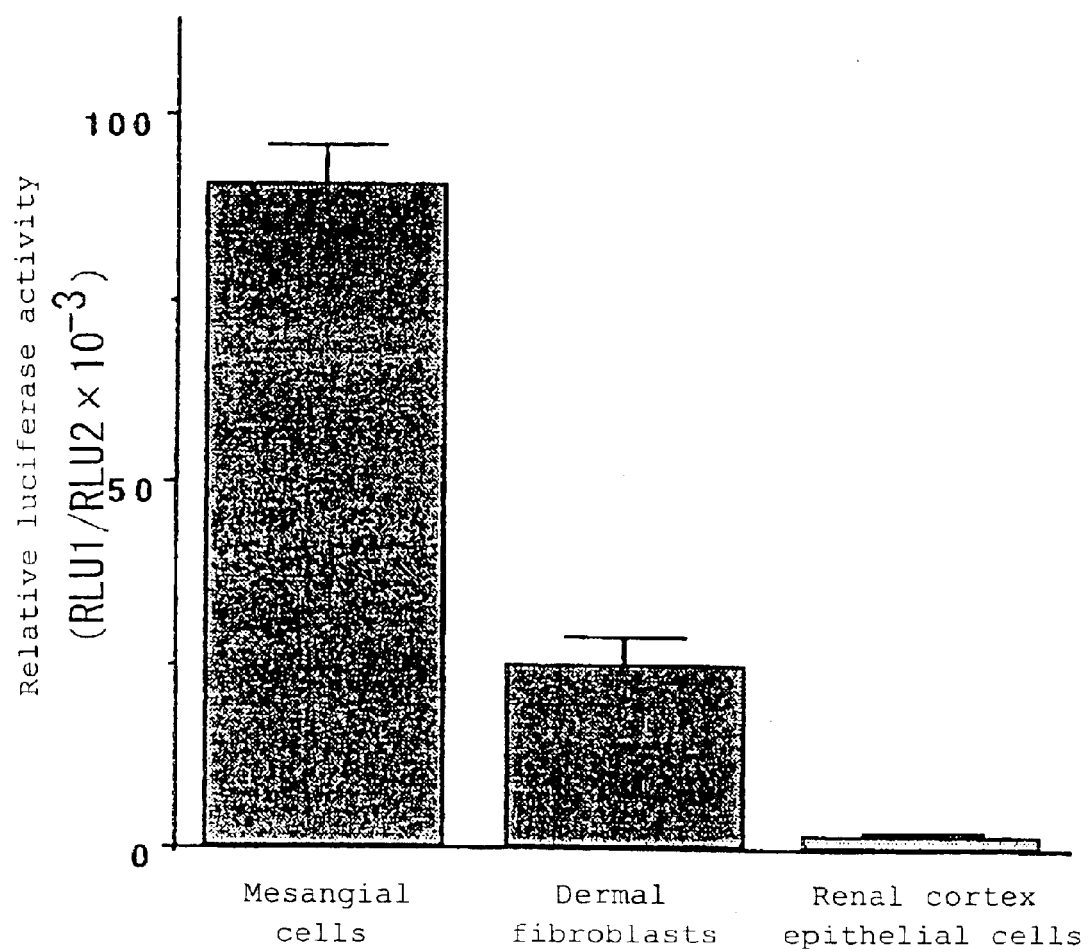

FIG. 5 shows the results of luciferase assay of transcription regulatory region of human MEGSIN gene using various cells. The relative activity of the promoter normalized with that of β-galactosidase is shown.

Figure 6:
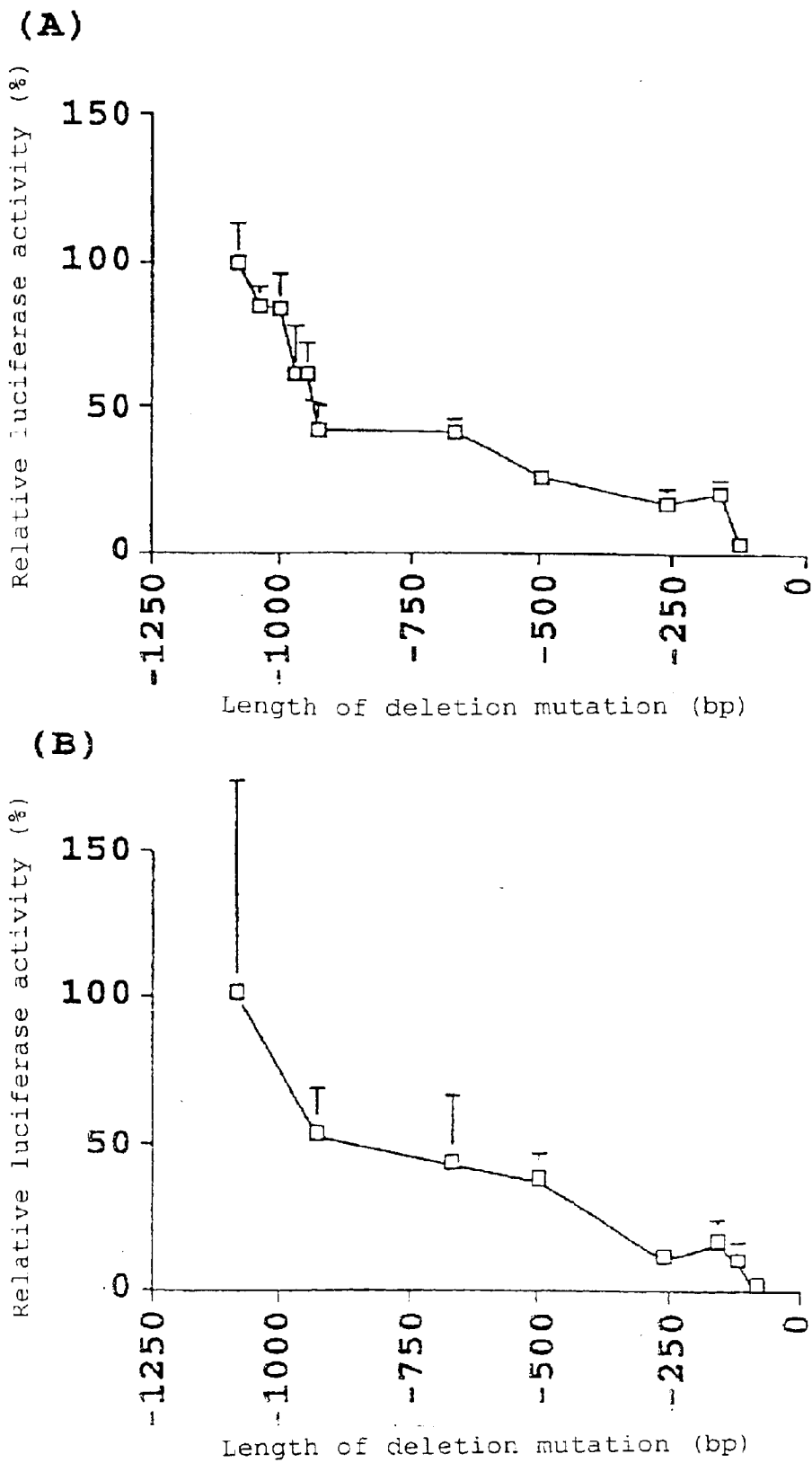

FIG. 6 shows the results of luciferase assay of deleted transcription regulatory region of human MEGSIN gene. The relative activity of the promoter normalized with that of β-galactosidase is shown (the value is 100 when the region is not deleted). (A) shows the results of human epidermoid tumor cell line A431, and (B) shows the results of human mesangial cells.

Figure 7:
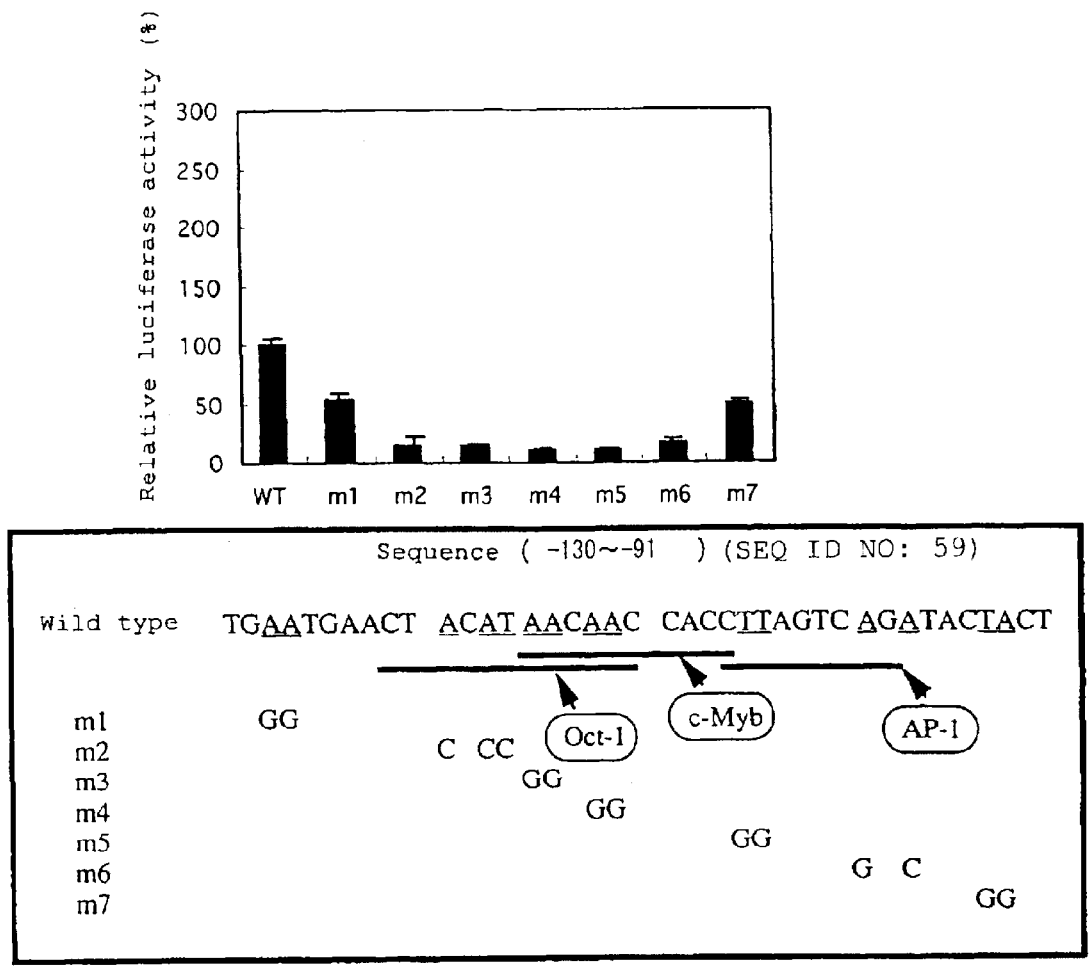

FIG. 7 shows the results of luciferase assay of transcription regulatory region of human MEGSIN gene in which the site-specific mutation was introduced. The lower panel shows the mutation introduced, and the upper panel shows the relative activity of the promoter normalized by that of β-galactosidase (the value is 100 when the region is not deleted). The binding sites of Oct-1, c-Myb, and AP-1 are also shown in the lower panel.

FIG. 8 shows the results of gel shift assay using transcription regulatory region (from −129 to −89) of human MEGSIN gene. The upper panel indicates the DNA sequence of the probe, and the lower panel indicates the results.

Figure 9:
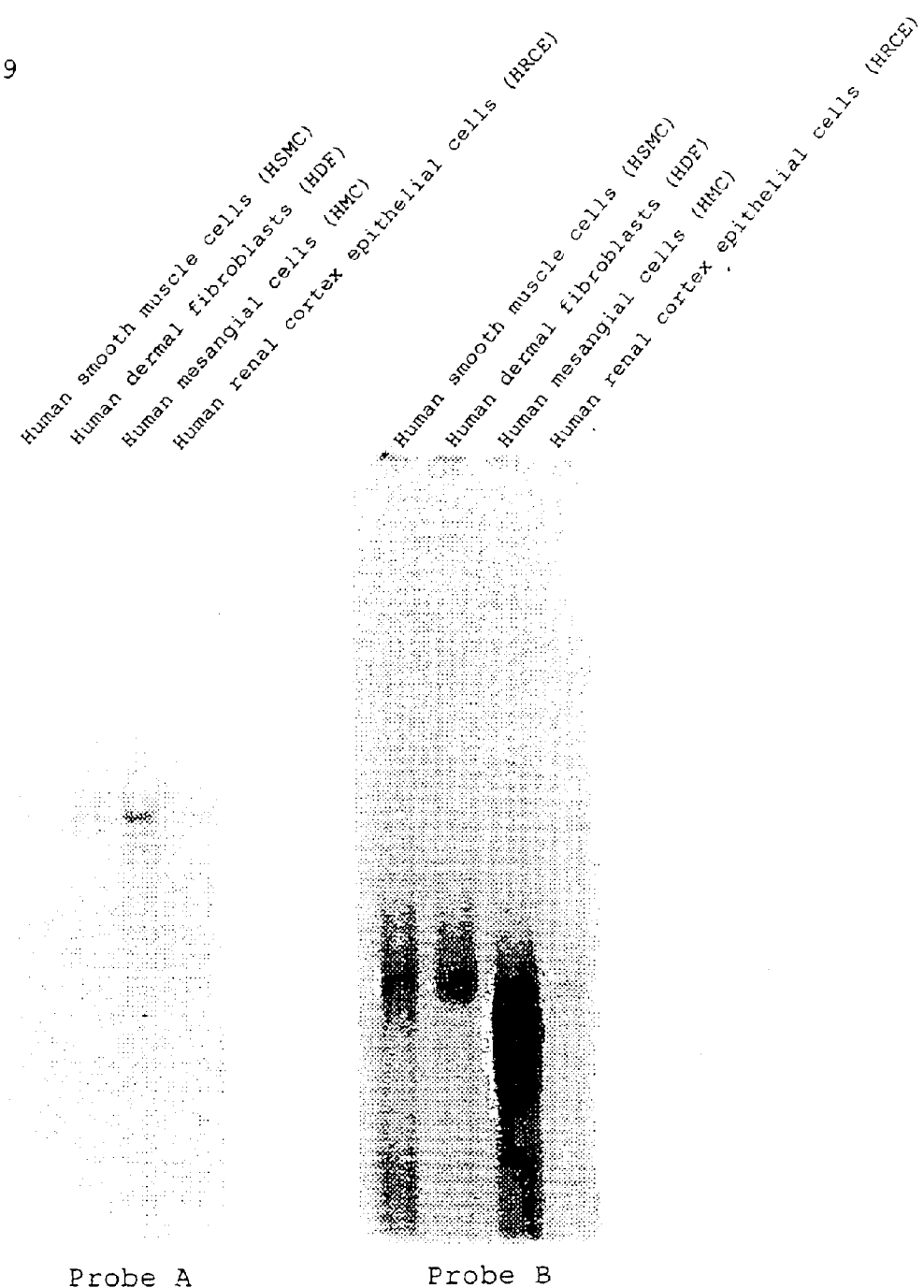

FIG. 9 is the photograph showing the results of gel shift assay of the transcription regulatory region (from −129 to −89) of human MEGSIN gene using various primary cells extracts from human. Probes A and B described in FIG. 8 were used.

BEST MODE FOR CARRYING OUT THE INVENTION

The present invention is illustrated in detail below with references to examples, but is not to be construed as being limited thereto.

EXAMPLE 1

Primary Culture of Human Mesangial Cells

Human renal mesangial cells (Clontech) were cultured in Dulbecco modified Eagle medium (DMEM) that includes 10% bovine fetal serum (GIBCO), 100 IU/mL penicillin, 100 μg/mL streptomycin, and 200 μg/mL L-glutamine.

EXAMPLE 2

Isolation of the Transcription Regulatory Region of Human MEGSIN Gene

The upstream region of human MEGSIN gene was isolated by Genome Walker Kits (Clortech). The upstream region of human MEGSIN gene was amplified by nested Polymerase Chain Reaction using a human genomic library of Genome Walker Kits as a template, MEGSIN specific primer (5'-CGTCGACGGACACGTCTCACGTCCGACG-3'/SEQ ID NO: 4) designed based on the MEGSIN cDNA sequence [Miyata, T. et al., J. Clin. Invest., 120, 828–836 (1998)], the adaptor primer attached in the kit, and PCR buffer. The genomic DNA of boundary between exon and intron were also isolated by the same manner.

Furthermore, highly conserved binding site sequences of transcription factors were searched by the analysis of TFMATRIX transcription factor binding site database (E. Wingender, R. Knueppel, P. Dietze, and H. Karas: GBF-Braunschweig) using TFSEARCH program (Yutaka Akiyama: Kyoto University).

As a result of the analysis of genomic DNA sequences, it has been revealed that human MEGSIN gene has 8 exons and 7 introns and that it is encoded over about 20 kb DNA. The exon-intron boundary regions (splicing sites) followed the GT-AG rule. The structures are shown in Table 1. Upper-case characters of the sequence indicate exons and lower-case characters indicate introns in Table 1.

TABLE 1

| No. | Exon (bp) | Intron (kbp) | Donor sequence | Acceptor sequence |
| --- | --- | --- | --- | --- |
| 1 | 346 | 6.0 | CTAGCgtgag | tctagGCTGC |
| 2 | 186 | 0.5 | ATAAGgtcag | tacagTTGCT |
| 3 | 51 | 0.9 | GTCAGgtaaa | aacagTCAGG |
| 4 | 117 | 3.3 | ATAAGgtaag | tatagGACTA |
| 5 | 118 | 3.0 | ACATGgtgag | aaaagGCAAA |
| 6 | 143 | 3.0 | CCAAGgtatg | ttcagTGCTC |
| 7 | 147 | 3.5 | CTGAAgtaag | tacagATTGA |
| 8 | 1141 | | | |

FIG. 1 shows the comparison between the nucleotide sequences of boundary region of exon-intron of human MEGSIN gene and that of plasminogen activator inhibitor type2 (PAI-2) gene [Ye, R. D., J. Biol. Chem., 264, 5495–5502 (1989)], which belongs to Serpin superfamily like MEGSIN. Because both sequences are highly conserved, it is revealed that both sequences are phylogenetically closely related to each other.

The nucleotide sequence of human MEGSIN gene promoter determined (from −1431 to −1) are shown in FIG. 2 and SEQ ID NO: 2. The nucleotide sequence of 5' untranslated region (5'-UTR) (from 1 to 181) is shown in FIG. 2 and SEQ ID NO: 3.

EXAMPLE 3

Fluorescent in Situ Hybridization (FISH)

Sample slides of chromosomes in metaphase from cultured lymphocytes from human peripheral blood stimulated with phytohemagglutinin (PEA) were constructed by the standard methods. DNA derived from F581 clones labeled with digoxigenin-dUTP by nick translation method was used as a probe for FISH. Labeled probes were mixed with 50% formamide, 10% dextran sulfate, and buffer including 2×SSC and then hybridized with the sample slides mentioned above. Sample slides hybridized were incubated with fluorescein-labeled anti-digoxigenin antibodies (Boehringer Mannheim). The specific hybridization signals were detected by counter staining using 4',6'-diamidine-2'-phenylindole dihydrochloride (DAPI). Sample slides were incubated with fluorescein-labeled anti-digoxigenin antibodies (Boehringer Mannheim) and texas red-labeled avidin (Boehringer Mannheim), and then the detection of probes by dichroic staining was done by counter staining using DAPI. As a result, it has been revealed that human MEGSIN gene is located at chromosome 18q21.3.

EXAMPLE 4

Identification of the Transcription Initiation Site by S1 Nuclease Protection Assay 5' end of human MEGSIN mRNA was determined by S1 nuclease protection assay [Berk, A. J. et al., Proc. Natl. Acad. Sci. USA., 75, 1979 (1978)] using poly(A)+ RNA extracted from human mesangial cells in Example 1.

Figure 3:
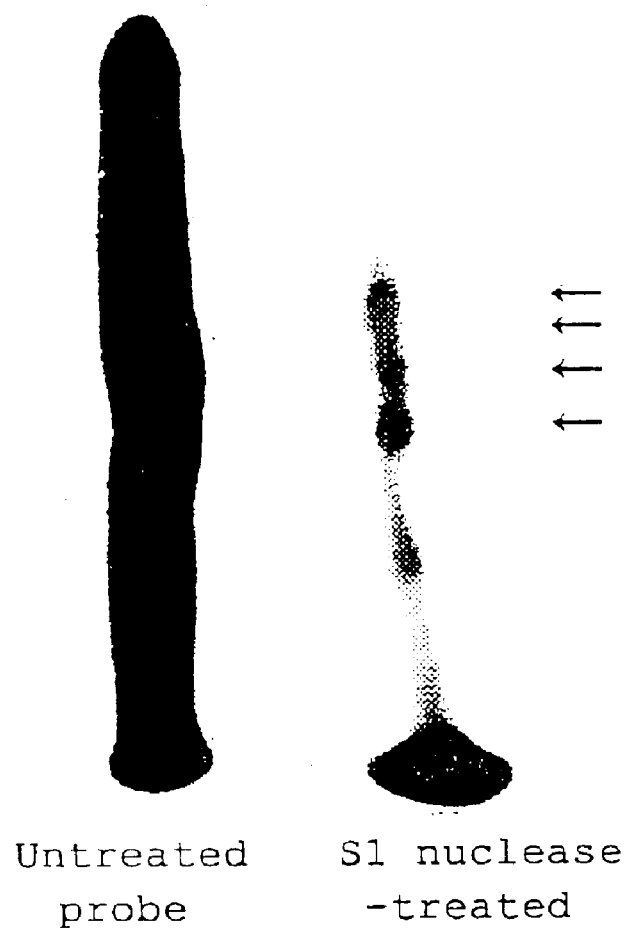
FIG. 3 is the photograph showing the results of S1 nuclease assay for determining the transcription initiation sites of human MEGSIN gene.

Labeled probes were prepared by multiprime method. The oligonucleotide primer (5'-ttccctgtac atgcacttag gaaggtgatg a-3'/SEQ ID NO: 5) corresponding to bp from +161 to +191 fully covering the initiation site was annealed with denatured MEGSIN promoter. Then, the primer was incubated with Klenow enzyme in buffer including [$^{32}$P]-dCTP at 37° C. for 15 minutes. The resultant was purified using Sephadex G-50 column (Pharmacia) and used as a radiolabeled probe. The probes were hybridized with 0.2 μg of mRNA prepared from cultured mesangial cells at 55° C. for 16 hours using S1-Assay kit (Ambion). To the DNA-RNA hybrid, 500 μg of S1 buffer containing S1 nuclease was added, and the solution was incubated at 37° C. for 30 minutes. The last product was electrophoresed and analyzed by autoradiography (FIG. 3).

As a result, it has been revealed that the first exon of human MEGSIN gene is 346 bp although there are three other transcription initiation sites. Moreover, transcription initiation sites were determined using total RNA of human mesangial cells as samples with 5'-RACE kit (Takara) following the protocol attached with the kit (FIG. 2).

As a result of the analysis of nucleotide sequences, conserved promoter regions including AP-1 binding site, cMyb binding site, and Oct-1 which can be transcription regulatory sites were found in the upstream region of MEGSIN gene. No consensus sequence of TATA box (Mol. Cell. Biol., 1, 281 (1981)] or CAAT box [Science, 236, 1237 (1987)] was found.

EXAMPLE 5

Functional Examination of MEGSIN Transcription Regulatory Regions

Figure 4:
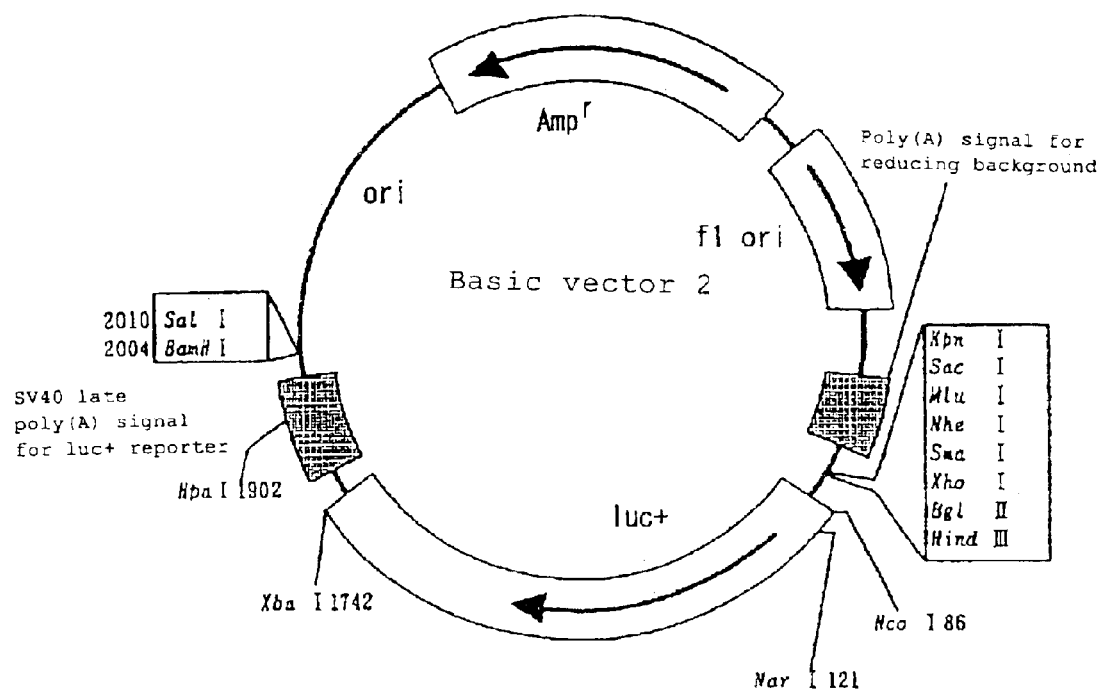
FIG. 4 shows the structure of the vector used for luciferase assay.

To examine transcription regulatory regions, vectors in which the upstream region of MEGSIN gene (KpnI-DraI fragment: from −1154 to +59) or its deletion mutant and luciferase gene were lagated were prepared. Various deletion mutant DNAs were prepared by polymerase chain reaction (PCR) using paired primers covering the region used for the assay. Specifically, deletion mutant DNA including the region from −1079 to +59, from −1040 to +59, from −1000 to +59, from −940 to +59, from −927 to +59, from −669 to +59, from −497 to +59, from −258 to +59, from −158 to +59, from −128 to +59, from −121 to +59, or from −97 to +59 of MEGSIN gene was constructed using primer 13 (5'-aggctgtccaaaggtgcagcctgcactctg-3'/SEQ ID NO: 18) as an antisense primer and primer 1 (5'-ggtaccttctaattccaatagctttttac-3'/SEQ ID NO: 6), primer 2 (5'-ccagttacttggataaatgttggctgtact-3'/SEQ ID NO: 7), primer 3 (5'-ctcaggcagaaggaccaggcttgcagtcat-3'/SEQ ID NO: 8), primer 4 (5'-acatacagctcaacctcatgatgctacggc-3'/SEQ ID NO: 9), primer 5 (5'-cctcatgatgctacggccagaaactgaaat-3'/SEQ ID NO: 10), primer 6 (5'-ccaagtttcagctcctatctgaagctgctc-3'/SEQ ID NO: 11), primer 7 (5'-ggtccagatgaaaatctgagattggagaat-3'/SEQ ID NO: 12), primer 8 (5'-atgtcttgacccaggctgacagatactgtt-3'/SEQ ID NO: 13), primer 9 (5'-cctcctgaaatctgattcacatacaaactg-3'/SEQ ID NO: 14), primer 10 (5'-aatgaactacataacaaccaccttagtcag-3'/SEQ ID NO: 15), primer 11 (5'-tacataacaaccaccttagtcagatactac-3'/SEQ ID NO: 16), or primer 12 (5'-tactactttgaaacctggttcaaaacctaa-3'/SEQ ID NO: 17) as a sense primer, respectively. Multi cloning site of luciferase expression vector (Picca Gene Basic Vector 2: Toyo Inki) (FIG. 4) was digested with KpnI and HindIII, and the above PCR product was inserted into the vector. The vector was introduced into a cell using LiopfectAmine (Gibco-BRL) following the attached protocol.

At first, vectors having the upstream region of MEGSIN gene (from −1154 to +59) in which no deletion was introduced were transformed into various cells, and the specificity of the transcription activity depending on the kinds of cell was examined (FIG. 5). Vectors were transfected at 37° C. for 5 hours [Derijard, B. et al., Cell, 76, 1025–1037 (1994)]. After incubation at 37° C. for 2 days, culture medium was removed, and the cells were washed 3 times with PBS. Lysate was obtained by lysing with cell lysis buffer. Cell lysate was centrifuged and cell debris were precipitated and removed. The amount of the fluorescence was measured directly by using Lumat LB9507 luminometer (EG&G Berthold). The relative luciferase activity was obtained by dividing the amount of light emitted by β-galactosidase activity that was measured by the absorbance at 570 nm wavelength [Herbome, P. et al., Cell, 39, 653–662 (1984)]

Human cultured mesangial cells described in Example 1 (Clontech), human dermal fibroblast (HDF: Takara), and human renal cortex epithelial cells (HRCE: Takara) were used as the cells. As a result, luciferase activity was observed specifically in human cultured mesangial cells (FIG. 5). Thus, it was revealed that the transcription regulatory region used had the specificity for musangial cells.

Secondly, various DNAs having deleted mutations were treated in the above manner, integrated into vectors, and transfected into human epidermoid cell strain A431, or human cultured mesangial cells in Example 1 (Clontech). Then, the luciferase activity was measured. The results are shown in FIG. 6. The graph shows the relative value in the case where the value is 100% when no deletion was introduced at the upstream region of MEGSIN gene.

Because the transcription activity decreased to about 60% when the region from −1154 bp to −941 bp was deleted, it was shown that the sequence that controlled the transcription positively existed in this region. Almost no decrease of transcription activity was observed when the region to −159 bp was deleted. However, the transcription activity decreased by 5% when the region from −158 bp to −121 bp was deleted, compared to the existence of whole region. Because the transcription activity decreased dramatically when the region from −128 bp to −121 bp was deleted, the region from −128 bp to −121 bp can be thought to be important in positive regulation of transcription.

Because the region from −129 to −90 contains AP-1 (activating protein 1) binding sequence (cttagtcaga) [Lee, W. et al., Nature, 325, 368–372 (1987), Foletta, V. C. et al., J. Leuk. Biol., 63, 139–152 (1998)], c-Myb binding sequence (aacaaccacc) (13th to 22nd positions in SEQ ID NO: 1), and Oct-1 binding sequence (ctacataacaac) (7th to 19th positions in SEQ ID NO: 1) [Rosenfeld, M. G. et al., Genes Dev., 5, 897–907 (1991)], which are transcription regulatory factor binding sequence, the existence of transcription regulatory sites in this region was suggested.

For further examination whether this region was involved in the transcriptional activation of MEGSIN gene, mutations were introduced into various sites in this region and the effect for the transcription activity was examined. Specifically, to examine the changes of potential of transcription regulatory domain caused by the introduction of mutation to the specific nucleotides, various mutants in which the positions from −128 to −127 was mutated to gg (m1), the positions from −120 to −117 to cccc (m2), the positions from −116 to −115 to gg (m3), the positions from −113 to −112 to gg (m4), the positions from −106 to −105 to gg (m5), the positions from −100 to −98 to ggc (m6), and the positions from −94 to −93 to gg (m7) were constructed by using Quick Change site-directed mutagenesis kit (Stratagene) following the attached manual.

Construction of these mutants was confirmed directly by performing dideoxy nucleotide sequencing. These mutants were integrated into vectors, and the luciferase activity was obtained in the above manner. As a result, luciferase activity of m3–m7 decreased dramatically (FIG. 7). The graph in the Figure shows the relative value in the case where the value is 100% when no deletion was introduced at the upstream region of MEGSIN gene.

EXAMPLE 6

Search for Promoter Binding Proteins

Because it was revealed in Example 3 that the region downstream (3' end) of −128th position had the activity to control the transcription positively, proteins (transcription factors) binding to this region were detected by gel shift assay using two kinds of probes [probe A (5'-GAATGAACTACATAACAACCACC-3'/SEQ ID NO: 19; the region from −129 to −107) and probe B (5'-AACCACCTTAGTCAGATACTACTTT-3'/SEQ ID NO: 20; the region from −113 to −89)].

Terminal of each probe was labeled by the standard method. Then, a nuclear extract from mesangial cells of Example 1 was prepared by the method of Dignam et al. [Dignam, J. et al., Nucleic Acid Res., 11, 1475–1489 (1983)] followed by the DNA-protein binding reaction in the reaction mixture containing 10% glycerol, 5 mM magnesium chloride, 1 mM EDTA, 25 mM dithiothreitol, 50 mM potassium chloride, 10 mM Hepes-KOH, 3 µg poly(dI-dC), 7 µL nuclear extract, and labeled probe at room temperature for 30 minutes. After the reaction, electrophoresis and autoradiography were done. As a result, band shift of DNA-protein complex was observed for each probe, and two kinds of transcription factors were identified (FIG. 8).

To investigate whether the mesangial cell-specific expression of MEGSIN is affected by the amount of the transcription factors recognizing this region, the gel shift assay was done for the comparison using human cultured mesangial cells described in Example 1 (Clontech), human smooth muscle cells (HSMC: Takara), human dermal fibroblast (HDF: Takara), and human renal cortex epithelial cells (HRCE: Takara). As a result, it was revealed that the amount of DNA-protein complex was larger specifically in the human cultured mesangial cells for all probes (FIG. 9). This shows that the mesangial cell-specific expression of MEGSIN is affected by the transcription factors recognizing this region.

Industrial Applicability

The present invention provides a promoter of MEGSIN gene, expressed specifically in mesangial cells. The promoter of this invention can be used for the expression of the gene specifically in mesangial cells, and it is also applicable to, for example, gene therapy of various renal diseases. This is also available for the screening of proteins such as transcription factor that binds to the promoter.

What is claimed is:

1. A method of screening for a protein that binds to a nucleotide sequence consisting of from 23 to 41 continuous nucleotides of SEQ ID NO:60 positions 2 to 42, comprising the steps of:
   providing the nucleotide sequence;
   contacting the nucleotide sequence with a sample; and
   selecting a protein which binds to the nucleotide sequence.

2. The method of claim 1, wherein the protein is a transcription factor.

3. The method of claim 1, wherein the nucleotide sequence is chosen from SEQ ID NO.:19 and SEQ ID NO.:20.

4. An isolated nucleotide sequence consisting of from 23 to 41 continuous nucleotides of SEQ ID NO.:60 positions 2 to 42.

5. The isolated nucleotide sequence as claimed in claim 4, wherein the sequence is chosen from SEQ ID NO.:19 and SEQ ID NO.:20.

* * * * *